(12) United States Patent
Mantovani

(10) Patent No.: US 11,090,488 B2
(45) Date of Patent: Aug. 17, 2021

(54) DEVICE AND METHOD FOR THE TREATMENT OF JOINT INSTABILITY

(71) Applicant: NCS LAB S.R.L., Carpi (IT)

(72) Inventor: Matteo Mantovani, Carpi (IT)

(73) Assignee: NCS LAB S.R.L., Carpi (IT)

( * ) Notice: Subject to any disclaimer, the term of this patent is extended or adjusted under 35 U.S.C. 154(b) by 77 days.

(21) Appl. No.: 16/512,974

(22) Filed: Jul. 16, 2019

(65) Prior Publication Data

US 2020/0023181 A1 Jan. 23, 2020

(30) Foreign Application Priority Data

Jul. 17, 2018 (IT) .................. 102018000007252

(51) Int. Cl.
*A61N 1/36* (2006.01)
*A61B 5/107* (2006.01)
*A61B 5/11* (2006.01)

(52) U.S. Cl.
CPC ........ *A61N 1/36003* (2013.01); *A61B 5/1071* (2013.01); *A61B 5/1114* (2013.01); *A61B 5/1122* (2013.01); *A61N 1/36031* (2017.08); *A61B 2562/0219* (2013.01); *A61B 2562/0223* (2013.01)

(58) Field of Classification Search
None
See application file for complete search history.

(56) References Cited

U.S. PATENT DOCUMENTS

| 8,165,685 | B1* | 4/2012 | Knutson | A61N 1/36003 |
| | | | | 607/48 |
| 2002/0161415 | A1 | 10/2002 | Cohen et al. | |
| 2005/0171577 | A1 | 8/2005 | Cohen et al. | |
| 2017/0036015 | A1* | 2/2017 | Gozani | A61B 5/486 |
| 2017/0106189 | A1 | 4/2017 | Keller et al. | |
| 2017/0224985 | A1* | 8/2017 | Debur | A61B 5/4836 |
| 2017/0303849 | A1 | 10/2017 | De Sapio et al. | |
| 2018/0160966 | A1 | 6/2018 | Inan et al. | |

* cited by examiner

*Primary Examiner* — Brian T Gedeon
(74) *Attorney, Agent, or Firm* — Pearne & Gordon LLP

(57) ABSTRACT

The device (1) for the treatment of joint instability and dyskinesia comprises: an inertial sensor (11, 12) for detecting the movements of a limb (2) of a person, adapted to produce movement signals; an electrostimulation element (14) that can be positioned at a predetermined point of the patient's body so as to electrically stimulate muscles involved in the movement of the limb (2); a waveform generator (15) for supplying the electrostimulation element (14); and a processing means (4) connected to the inertial sensor (11, 12) and to the generator (15), comprising: a position module (41) configured to determine positions of the limb (2) on the basis of the movement signals; and a stimulation module (42) configured to produce stimulation signals adapted to control the operation of the generator (15), on the basis of one or more positions of the limb (2) determined by the position module (41).

19 Claims, 2 Drawing Sheets

DEVICE AND METHOD FOR THE TREATMENT OF JOINT INSTABILITY

The present invention relates to a device and a method for the treatment of joint instability, with particular, but not exclusive, reference to instability of the shoulder and dyskinesia, i.e. an alteration of the scapulohumeral rhythm.

The term 'shoulder instability' is used to refer to the inability to maintain the humeral head in the glenoid fossa.

The people who are affected by it may show various functional symptoms, which go from a sensation of instability or a loose shoulder to pain during certain movements or even a loss of the range of movement.

The humeral head translates excessively, provoking a subluxation or dislocation when the shoulder passes through a particular phase of movement.

The common symptoms reported are pain during arm movement, loss in the range of movement and a strong sensation of instability which largely limits shoulder function.

Various studies have confirmed that inappropriate models of muscular activation can contribute or lead to glenohumeral instability.

The studies have demonstrated that patients with an abnormal muscular model and the resulting posterior shoulder instability show an underactivity of the external rotators and scapular retractor muscles, including the infraspinatus, the lower trapezius, the serratus anterior and the posterior deltoid.

Physiologically, the humeral head is centred by the rotator cuff and the periscapular muscles during movement, thus preventing subluxation or dislocation.

However, when the external rotators are hypoactive during elevation of the arm whilst the internal rotators, including the latissimus dorsi and the pectoralis major and the anterior deltoid, show a normal or even greater activity, an imbalance of forces is provoked, which causes the humeral head to translate posteriorly.

This translation is associated with pain, limited movement and/or posterior dislocation.

Furthermore, these patients often show alterations in scapular movement and impairment of the scapulothoracic rhythm.

In addition to limitations during sports activities or even activities of everyday life, these patients often suffer from emotional stress and are often stigmatised because of their conditions.

It is generally accepted among shoulder surgeons that surgical treatment is not indicated.

At present, for this type of pathology, the treatment that leads to the main improvement in patients is a conservative treatment.

In fact, a certain degree of success in the conservative treatment of these patients has been reported by highly specialised physiotherapy units; however, the regular physical therapy and muscle exercise therapy available today do not provide full effectiveness.

Therefore, for some time a need has been felt for a treatment for the rehabilitation of shoulder instability which overcomes the limits of the prior art.

The technical task at the basis of the present invention is thus to propose a device and a method for the treatment of shoulder instability which satisfies the above-mentioned need.

Said technical task is achieved by the device and the method conceived in accordance with the claims.

Additional features and advantages of the present invention will become more apparent from the approximate, and thus non-limiting, description of preferred but not exclusive embodiments of the device of the invention, as illustrated in the appended drawings, in which.

Figure 1:
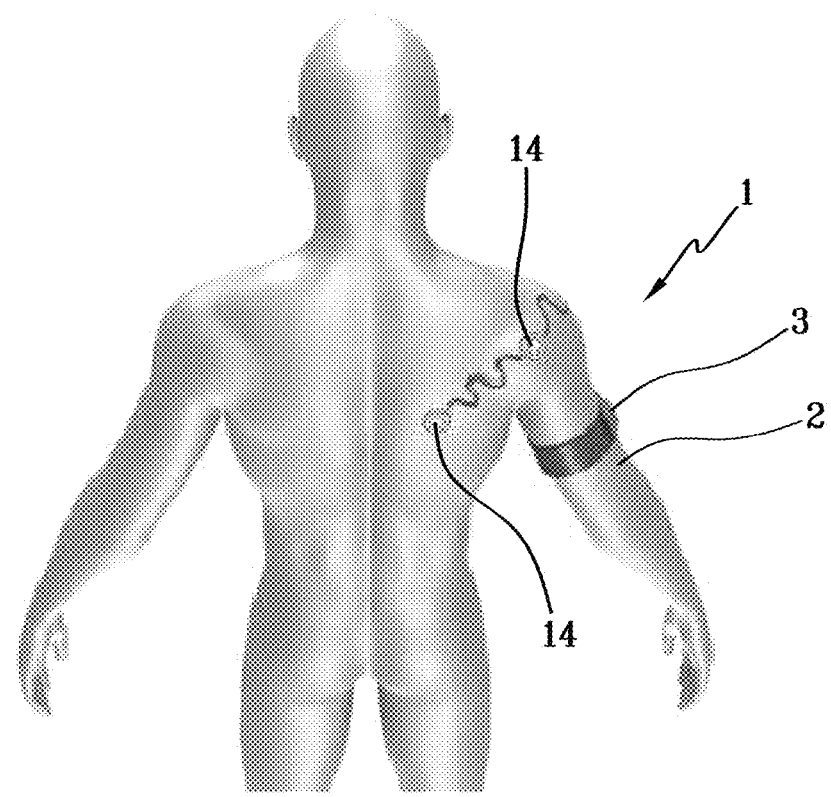
FIG. 1 is schematic view of the device applied to a person represented in a stylised manner.
Figure 2:
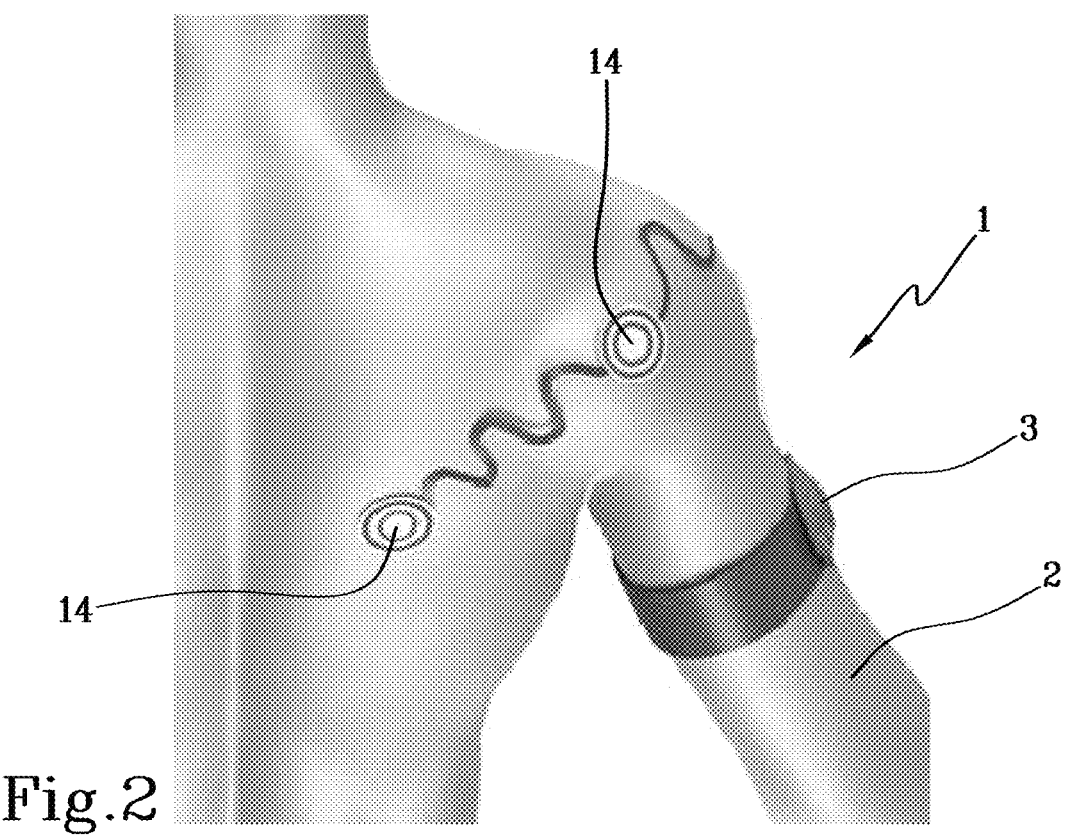
FIG. 2 is an enlarged detail of the preceding figure.
Figure 3:
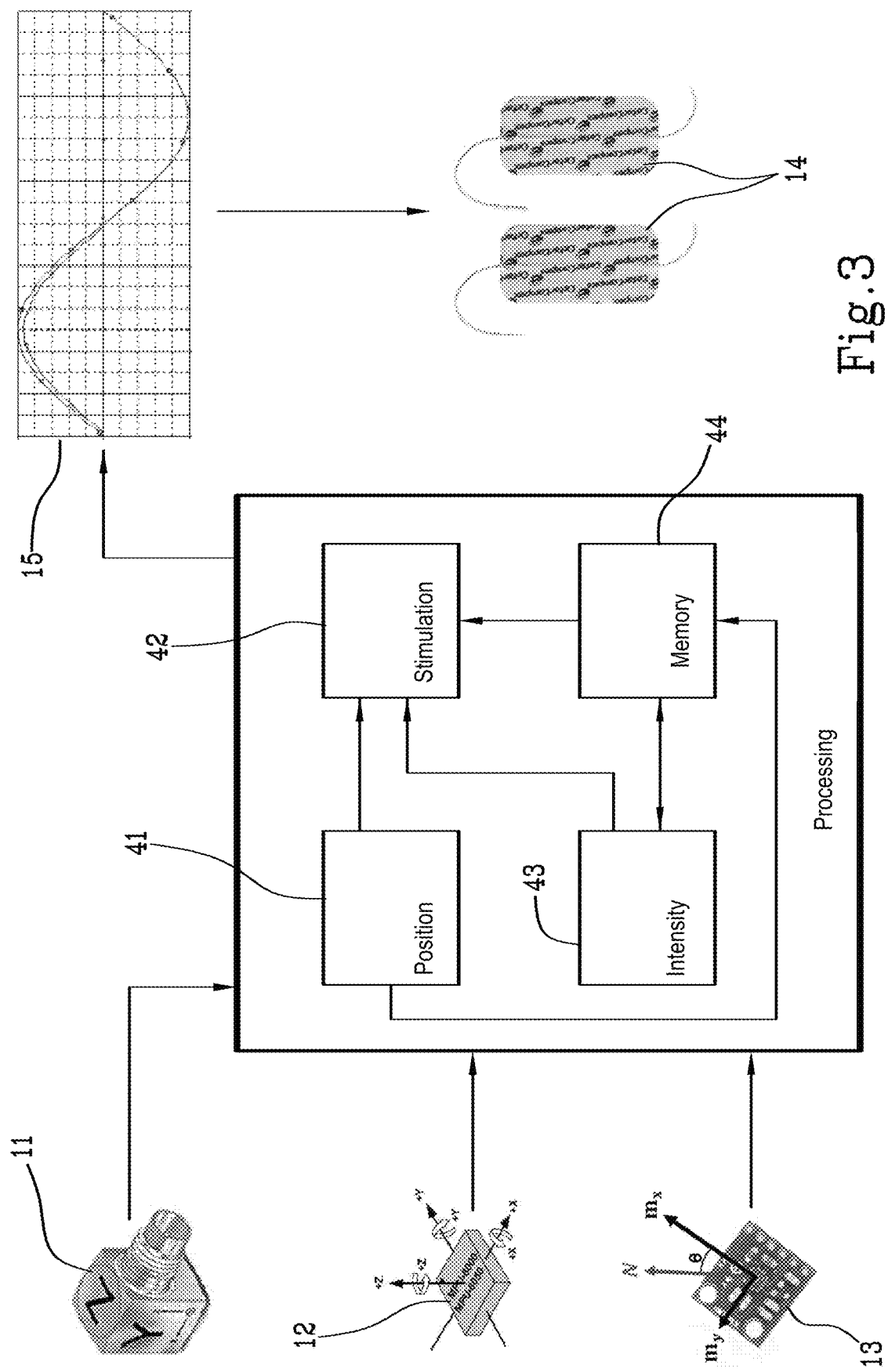
FIG. 3 is a diagram of the processing unit of the invention.

With reference to the aforesaid figures, the number 1 denotes a device for the treatment of the joint instability realised in accordance with the invention.

The device 1 has been designed to prevent joint instability, for example, with reference to the arm 2, the eventuality of the humeral head coming out of the glenoid fossa, and it has further been conceived to bring about, with use, a cure for or strong reduction in instability.

Although frequent mention will be made below to the use of the invention to treat shoulder instability, this does not rule out the use thereof for the treatment of instability of other joints such as the knee, ankle and hip.

The device 1 proposed comprises first of all at least one inertial sensor 11, 12 for detecting the movements of a limb 2 of a person, which sensor 11, 12 is adapted to produce movement signals, indicative of the position that the limb 2 itself assumes, instant by instant.

In practical terms, it is possible to use triaxial inertial sensors as accelerometers 11 and gyroscopes 12, associating them with the limb 2, and thereby detecting the position of the latter relative to a predetermined reference system.

For example, it may be decided to use a reference system with the centre preferably in the shoulder, for example the glenoid fossa itself, and use the inertial sensors 11, 12 to establish an angle of spatial rotation assumed by the humerus, information that will then be used by the device 1 in the ways explained below.

By way of non-limiting example, said angle can be calculated by means of quaternions.

The device 1 can also include a magnetometer 13 adapted to produce orientation signals, indicative of the orientation of the limb 2 relative to the earth's magnetic field.

The purpose of the magnetometer 13 is to provide an indication of the starting orientation of the limb, in particular to indicate when the patient is standing with his or her arm positioned vertically.

The device 1 of the invention further includes at least one electrostimulation element 14 that can be positioned at one point of the patient's body so as to electrically stimulate muscles involved in the movement of the limb 2 to be treated.

In practical terms, the device 1 can include one or more electrodes 14, for example two, as in the embodiment illustrated in the figures, which are applied on the skin near the muscles to be stimulated, for example by adhesive means.

It should be noted that the aforementioned inertial sensors 11, 12 can be solidly secured to the limb 2, for example inserted in an armband 3 in the case of instability of the humerus, or they can be mounted at the site of the electrodes 14, for example inside the same protective casing, so as to define integrated units, or else positioned in other parts of the body.

The device 1 further includes a waveform generator 15 connected to the electrostimulation elements 14 in order to supply them with sequences of electric pulses selected so as to appropriately stimulate the target muscles.

According to an important aspect of the invention, the proposed device 1 includes a processing means 4, connected to the inertial sensors 11, 12, the generator 15 and the magnetometer 13, comprising:

- a position module 41 configured to determine positions of the limb on the basis of the movement and orientation signals emitted by the sensors; and
- a stimulation module 42 configured to produce stimulation signals that are adapted to control the operation of the generator 15 and are produced on the basis of one or more positions assumed by the limb 2 and determined by the position module 41.

Conceptually, the stimulation of the muscles depends on the movement of the limb 2, in the sense that it is carried out on the basis of evaluations performed on the positions assumed by the limb, according to different possible embodiments which will be detailed below.

In practical terms, one of the ideas at the basis of the invention is to stimulate the hypoactive muscles involved in the movement of the limb 2, such as, for example, the controllers of the scapula in the case of treatment of shoulder instability, based on the fact that, while performing a certain movement, the limb 2 assumes trigger positions that are potentially preludes to instability.

In other words, knowing the type of movement that can lead to dislocation, or in any case to shoulder instability for a given person, and knowing the portion of a trajectory of the arm 2 within which instability can occur, makes it possible to anticipate and prevent the latter by identifying a "trigger" or "threshold" position, for example a certain angle formed by the humerus in the reference system, which leads to the activation of the generator so that it stimulates the less active muscles, thereby preventing the head from coming out partially or totally from the respective fossa.

In more technical terms, the aforesaid position module 41 is preferably configured to calculate, in various positions of the limb 2, a characteristic angle formed by the latter relative to a predetermined reference.

In this case, the stimulation module 42 is configured to activate said generator 15 if the characteristic angle is greater than a predefined threshold angle.

It should be noted that, as already explained in part, the invention can include one or more integrated units which, besides including the respective electrodes and generators, can comprise the generator 16 and the processing means 4.

For example, two integrated units can be provided, which may also be connected to each other, to be applied in specific points of the patient's body.

The processing means 4 comprises a memory module 44 in which a trajectory of the limb 2 is recorded, the trajectory being defined by spatial coordinates that represent the positions determined by the positioning module.

The trajectory can be representative of movements of the limb 2 which, if performed under exertion, could lead to instability; in practical terms, the trajectory in question can be an average trajectory calculated as the average of the values of the coordinates of a plurality of actual trajectories followed by the arm 2 and detected by the sensors 11, 12, 13, or it can be a range of trajectories whose coordinates fall within a predefined volume.

In any case, the aforesaid threshold angle is selected so that the relative position of the limb 2 corresponds to a point of the trajectory that precedes a possible imbalance (or "dyskinesia"); when "angle" is spoken of in the present description, it may also be understood as an interval around a given angle, be it the threshold angle or the characteristic angle.

Therefore, if the humerus is not brought beyond the threshold angle, the generator 15 will not be activated and the wave sequence will not be started; if, however, the threshold is exceeded, the processing means 4 will recognise the trigger condition and activate the production of a sequence of electric waves whose distribution (frequency, duration and rhythm) and form are selected on the basis of treatment parameters such as: specific muscles to be stimulated and individual variables of the person to be treated, detected by means of the device 1 in a learning or calibration step that will described below.

The processing means comprises a processing unit 4 which can be a microcontroller placed on board the device 1, for example associated with one of the electrodes 14 or the aforesaid armband 3, etc. . . . .

More in general, it should be noted that, in the present description, the processing unit 4 is presented as being split into distinct functional modules for the sole purpose of describing the functionalities thereof in a clear and complete manner.

In practical terms, the processing unit 4 can also consist of a single electronic device, conveniently programmed to perform the functionalities described, and the different modules can correspond to hardware entities and/or routine software that are part of the programmed device.

Alternatively, these functions can be performed by a plurality of electronic devices over which the above-mentioned functional modules can be distributed.

In general, the processing unit 4 can rely on one or more microcontrollers or microprocessors to execute the instructions contained in the memory modules and, furthermore, the above-mentioned functional modules can be distributed locally or remotely based on the architecture of the network in which they reside.

The processing unit 4 can include an intensity module 43, to which the stimulation module 42 is subject, configured to regulate the intensity of the current applied by the electrodes 14 automatically; in addition or alternatively, the proposed device 1 can comprise a manual adjustment means adapted to enable a user to adjust the intensity of the electrical signal, for example by means of a knob or an index on a touchscreen or other interface.

Furthermore, information on the current intensity to be used with a certain patient can be contained in the memory unit 44.

This value is a function of the maximum intensity that can be withstood by that patient; for example, it can be equal to the value of the tolerance threshold, or the value of the tolerance threshold reduced by a marginal amount; the latter could be fixed or variable.

In detail, every time it is used again, the device 1 can set itself automatically to the maximum intensity value that was established during one or more previous uses, in which the tolerance threshold was determined and acquired.

Said value can change, for example, if, during treatment, the patient shows to be able to tolerate a gradually increasing intensity; in this case, the memory module 44 will record the new value, acquired through a user interface means, and the intensity module 43 will work using the value that is stored in the memory.

According to a variant of the invention, the memory module 44 comprises a first trajectory representative of movements of the limb 2 performed without exertion such as to lead to instability and a second trajectory substantially representative of the same movements as the first trajectory performed under exertion and which could potentially give rise to instability.

In this case, the processing means 4 comprises a comparison module (not represented) for calculating deviations between the coordinates of the first and second trajectory, thereby determining trigger coordinates for the activation of the generator by the stimulation module 42.

In addition to the above-described device 1, the invention can preferably also include a separate electronic device, for example a PC or a smartphone or the like, configured to process and record data transmitted by the processing unit 4 of the device 1 via a two-way transmission means, preferably wireless.

In this manner it is possible to record all the uses of the device 1 on one or more persons, for example for scientific studies or to improve calibration or in any case as an aid to the physician in planning therapy.

It has been experimentally demonstrated that having a person repeat the movements which in his or her case can cause joint instability, while using the device 1 of the invention, leads to a reduction or elimination of instability, even after the device 1 itself has ceased to operate, since the subject develops an autonomous ability to activate the previously hypoactive muscles, in ways that "imitate" the artificial stimulation, thereby preventing the occurrence of instability.

Therefore, by using the device 1 of the invention, one obtains a real non-invasive therapy for joint instability.

The invention also presents itself as a method for the treatment of instability which includes steps corresponding to the operation of the proposed device 1, including the functions performed by the modules of the processing unit 4.

In a more general sense, the invention in question proposes a method for the treatment of scapular dyskinesia and the imbalance that occurs, in general, in association with a defect of a structural type.

A component of functional instability can in fact be associated with different pathologies, such as: lesions of the rotator cuff, various forms of instability associated with lesions either of the lip or the bone part or both, arthropathies, etc.

It should be noted that the method is of a non-invasive and non-surgical type; in fact, it envisages intervening by using microcurrents that are made to pass through the skin from the outer surface to the muscles to be stimulated.

The method includes a learning part, during which a recording is made, preferably by means of the device 1 of the invention, of the trajectory or the trajectories followed by the limb 2 which are the ones that, in the experience of the specific person, can lead to instability.

Therefore, in the case of shoulder instability, the person to be treated performs the movements known to be involved in dislocation or subluxation multiple times.

It is in this manner that the trajectory or the trajectories mentioned previously are recorded and the threshold position is identified, which is preferably characterised by a certain threshold angle, as already explained.

As already explained, the threshold angle is specific for a given person, just as the sequence of electrical waves for stimulating the muscles can be specific for the physical characteristics of that person.

Once this information has been read, one proceeds with electrostimulation in the ways illustrated in the description of the device 1, which will afterwards be repeated, thus generalising the application.

In practical terms, the method of the invention comprises the following steps:

determining, instant by instant, the position of a limb 2; and on the basis of one or more determined positions, stimulating hypoactive muscles that control the movement of said limb 2 with electrical waveforms, thereby preventing the instability of the limb 2 itself.

It should be noted that stimulation is performed by means of one or more electrostimulation elements 14 that come into contact with the skin's surface without altering it, much less perforating it.

If the limb is an arm 2 and the stimulated muscles are muscles external rotators of the shoulder and/or scapular retractor muscles or other hypoactive muscles, the electrostimulations are performed with a waveform sequence selected so as to control the shift of the humeral head within the range of movement.

As specified in the description of the device 1, the invention comprises acquiring, preferably at every use, the current value corresponding to the tolerance threshold of the patient, i.e. the maximum value that can be withstood.

The method thus envisages that, at every use, a current value will be used which is a function of the aforesaid maximum value and in practice can be equal to or slightly lower than the maximum value; the starting value is preferably equal to the maximum value that can be withstood minus a marginal value which can be of a fixed or variable entity.

This operation could be reiterated at every use, going gradually to raise the tolerance threshold and, consequently, the intensity of the current with which the device 1 is used.

The method of the invention comprises performing, during different sessions, electrical stimulation of the muscles involved a number of times during the performance of movements that may potentially give rise to instability; this step, as already explained, leads to the development of a natural activation of the muscles, once the artificial electrical stimulation thereof is interrupted.

In practical terms, the invention envisages that, once the learning step is over, the patient will carry out a sort of "self-rehabilitation", in the sense that, despite being monitored by a physician to verify the correct implementation of the protocol, the patient will carry out the rehabilitation activities on his or her own, simply by wearing the proposed device 1.

The application of the electrostimulation elements 14 on the surface of the skin, as envisaged by the treatment method of the invention, is an operation that can be performed by a paramedic.

The invention claimed is:

1. A device for the treatment of shoulder instability and respective dyskinesia, comprising:
   at least one inertial sensor for detecting the movements of an arm of a person, adapted to produce movement signals;
   at least one electrostimulation element that can be positioned at a predetermined point of the patient's body so as to electrically stimulate muscles which are controllers of a scapula of the patient, involved in the movement of said arm; at least one waveform generator for supplying said electrostimulation element; and
   a processing means connected to said inertial sensor and to said generator, the processing means comprising:
   a position module configured to determine positions of said arm on the basis of said movement signals and configured to calculate, in different positions of the arm, a characteristic angle formed by the latter relative to a predetermined reference; and a stimulation module configured to produce stimulation signals adapted to control the operation of said generator, on the basis of one or more positions of the arm determined by said position module;

wherein the stimulation module is configured to activate said generator if the characteristic angle is greater than a predefined threshold angle.

2. The device according to claim 1, wherein the inertial sensor has three axes.

3. The device according to claim 1, comprising one or more of the following inertial sensors: accelerometer and gyroscope.

4. The device according to claim 1, comprising a magnetometer adapted to produce orientation signals, wherein said position module is configured to determine positions of the arm also on the basis of said orientation signals.

5. The device according to claim 1, comprising at least one unit incorporating one or more of said sensors and said electrostimulation element.

6. The device according to claim 1, wherein the processing means comprises at least one memory module, in which at least one trajectory of the arm is recorded, defined by spatial coordinates that represent the positions determined by the position module.

7. The device according to claim 6, wherein said memory module comprises at least a first trajectory representative of movements of the arm performed without exertion such as to lead to an instability and a second trajectory substantially representative of the same movements as the first trajectory performed under exertion, the processing means comprises a comparison module for calculating deviations between the coordinates of said first and second trajectory, thereby determining trigger coordinates for the activation of the generator by the stimulation module.

8. The device according to claim 5, wherein said threshold angle is selected so that the relative position of the arm corresponds to a point of said trajectory which precedes a possible joint instability.

9. The device according to claim 1, comprising a manual adjustment means adapted to enable a user to adjust the intensity of the electrical signal produced by the electrostimulation element.

10. The device according to claim 1, wherein said stimulation signal is adapted to determine a stimulation of hypoactive muscles that control the movement of the arm, in order to avoid the instability thereof.

11. A system for the treatment of joint instability, comprising at least the device according to claim 1, whose processing means is connected, via a two-way transmission means, to a separate electronic device configured to process and record data.

12. A method for the treatment of joint instability, comprising:
determining, instant by instant, the position of a limb;
on the basis of one or more determined positions, stimulating hypoactive muscles that control the movement of said limb with electrical waveforms, thereby preventing the instability of the limb itself;
recording at least one trajectory of the limb, the trajectory being defined by spatial coordinates that represent the positions assumed by the limb itself, and
identifying a threshold point of said trajectory on the part of the limb, which, upon being reached, triggers the performance of the stimulation of said muscles,
wherein the stimulation is performed by means of one or more electrostimulation elements that come into contact with a surface of skin of the limb.

13. The method according to claim 12, wherein the limb is an arm and the stimulated muscles are muscles involved in the movement of the arm itself, the electrostimulations being performed with a waveform sequence selected so as to avoid instability or dyskinesia.

14. The method according to claim 12, wherein in the different positions of the limb, an angle formed by the latter in a predetermined reference system is calculated, the stimulation of the hypoactive muscles being performed if said calculated angle of the limb is greater than a predefined threshold angle.

15. The method according to claim 12, wherein said trajectory is chosen on the basis of the fact that it is susceptible, if followed under exertion, to lead the head of the humerus to come out of the glenoid fossa.

16. The method according to claim 12, comprising a step wherein at least a first trajectory representative of movements of the limb performed without exertion and such as to lead to instability is recorded along with a second trajectory representative of the same movements as the first trajectory performed under exertion and susceptible of producing instability, the method also including a step wherein a calculation is made of deviations between the coordinates of said first and second trajectory, thereby determining trigger coordinates for the activation of the electrostimulation of said muscles.

17. The method according to claim 12, comprising the step of acquiring a maximum current value that may be withstood by a patient, wherein at every use, the electrostimulation elements use a current whose intensity is based on said maximum acquired value.

18. A computer program that, when run on a processing means, performs the steps of the method according to claim 12.

19. A method for the treatment of shoulder instability, comprising the following steps:
determining, instant by instant, the position of an arm;
calculating a characteristic angle formed by the arm relative to a predetermined reference;
on the basis of one or more determined positions, stimulating hypoactive muscles with electrical waveforms if the characteristic angle is greater than a predefined threshold angle, thereby preventing the instability of the arm itself;
wherein the stimulation is performed by means of one or more electrostimulation elements that come into contact with the skin's surface.

* * * * *